(12) United States Patent
Sandberg

(10) Patent No.: US 6,310,252 B1
(45) Date of Patent: Oct. 30, 2001

(54) [(3-ALKOXY-PHENOXY)-ETHYL]-DIALKYLAMINE DERIVATIVES AND THEIR USE AS LOCAL ANAESTHETICS

(75) Inventor: Rune Sandberg, Järna (SE)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 08/776,620

(22) PCT Filed: Oct. 23, 1996

(86) PCT No.: PCT/SE96/01361

§ 371 Date: Jan. 27, 1997

§ 102(e) Date: Jan. 27, 1997

(87) PCT Pub. No.: WO97/15548

PCT Pub. Date: May 1, 1997

(30) Foreign Application Priority Data

Oct. 27, 1995 (SE) ................................... 9503798
Jan. 30, 1996 (SE) ................................... 9600329

(51) Int. Cl.$^7$ ............................................. A61K 31/135
(52) U.S. Cl. ........................................... 564/354; 514/651
(58) Field of Search ................... 564/348, 354; 514/651

(56) References Cited

U.S. PATENT DOCUMENTS

| | | | |
|---|---|---|---|
| 3,105,854 | 10/1963 | Druey et al. | 260/570.7 |
| 3,205,136 | 9/1965 | Tedeschi et al. | 167/65 |
| 3,221,054 | 11/1965 | Arnold et al. | 260/570.7 |

FOREIGN PATENT DOCUMENTS

| | | | |
|---|---|---|---|
| 103 252 | 3/1984 | (EP) | A01N/39/00 |
| 1.173.136 | 2/1959 | (FR) | |
| 302M | 8/1960 | (FR) | |

OTHER PUBLICATIONS

English language abstract of Document AL1, WPI accession No. 84–069878/198412, Derwent World Patents Index, Dialog file 351.

International Search Report for International Application PCT/SE96/01361). (1996).

*Primary Examiner*—Samuel Barts
(74) *Attorney, Agent, or Firm*—Michael A. Sanzo; Pillsbury Winthrop LLP

(57) ABSTRACT

There is provided compounds of formula I,

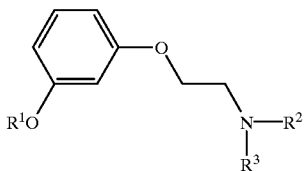

I wherein

R$^1$ represents C$_{3-5}$ alkyl; and

R$^2$ and R$^3$ independently represent C$_{1-3}$ alkyl; provided that when R$^2$ and R$^3$ both represent ethyl, then R$^1$ does not represent n-butyl, i-butyl or n-pentyl;

or a pharmaceutically acceptable salt thereof, which are useful as anaesthetics, in particular local anaesthetics and especially topically applied local anaesthetics.

30 Claims, No Drawings

[(3-ALKOXY-PHENOXY)-ETHYL]-DIALKYLAMINE DERIVATIVES AND THEIR USE AS LOCAL ANAESTHETICS

CROSS REFERENCE TO RELATED APPLICATIONS

The present application represents U.S. national stage of international application PCT/SE96/01361, with an international filing date of Oct. 23, 1996. The international application was published in English under Article 22(2) of the PCT on May 1, 1997. It claims priority to Swedish application 9503798-2, filed on Oct. 27, 1995, and to Swedish application 9600329-8, filed on Jan. 30, 1996.

FIELD OF THE INVENTION

This invention relates to pharmaceutically useful compounds, in particular [(3-alkoxy-phenoxy)-ethyl]-dialkylamine derivatives, their use as medicaments, in particular anaesthetics (e.g. local anaesthetics), pharmaceutical compositions containing them and synthetic routes to their production.

PRIOR ART

Certain [(4methoxy-phenoxy)-alkyl]-diethylamine derivatives are known as herbicides from European Patent Application 0 103 252. Their use as pharmaceuticals is not suggested.

Certain [(3- and [(4-alkoxy-phenoxy)-alkyl]-alkyl-propargyl and -cyclopropylamine derivatives are known to be useful in the treatment of psychiatric disorders from U.S. Pat. No. 3,221,054; and [(2,6-dimethoxy-phenoxy)-ethyl]-dimethylamine is known as an antidepressant from U.S. Pat. No 3,205,136. The compounds' use as anaesthetics is not suggested.

[(4-Alkoxy-phenoxy)-ethyl]-morpholine and -piperidine derivatives are known as local anaesthetics from French Patent No. 1 173 136. Moreover, certain 3-substituted phenoxyethylamine derivatives including (3-alkoxy-phenoxy)-ethyl]-diethylamine derivatives are known as local anaesthetics from U.S. Pat. No 3,105,854 and French Special Medicament Patent No. 302 M.

However, there remains a need for more effective anaesthetic compounds. Moreover there is a need particular need for effective local anaesthetics which may be administered topically to e.g. the skin.

We have found that certain compounds not specifically disclosed by, but included within, the scope of the specification of U.S. Pat. No 3,105,854 exhibit surprisingly good anaesthetic properties and are particularly useful as topical anaesthetics.

DISCLOSURE OF THE INVENTION

According to the invention there is provided a compound of formula I,

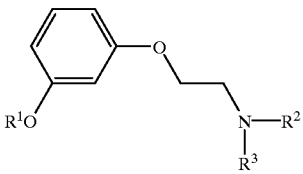

wherein $R^1$ represents $C_{3-5}$ alkyl; and $R^2$ and $R^3$ independently represent $C_{1-3}$ alkyl;

provided that when $R^2$ and $R^3$ both represent ethyl, then $R^1$ does not represent n-butyl i-butyl or n-pentyl;

or a pharmaceutically acceptable salt thereof (hereinafter referred to as "the compounds of the invention").

Pharmaceutically acceptable salts include nontoxic organic or inorganic acid addition salts, e.g. hydrochloride, hydrobromide, sulphate, hydrosulphate, nitrate, lactate, acetate, citrate, benzoate, succinate, tartrate, trifluoroacetate salts and the like. Preferred acid addition salts include hydrochloride salts.

The compounds of the invention may also contain one or more asymmetric carbon atoms and may therefore exhibit optical and/or diastereoisomerism. All diastereoisomer may be separated using conventional techniques, e.g. chromatography or factional crystallisation. The various optical isomers ray be isolated by separation of a racemic or other mixture of the compounds using conventional e.g. fractional crystallisation or HPLC, techniques. Alternatively the desired optical isomers may be made by reaction of the appropriate optically active starting materials under conditions which will not cause racemisation, or by derivatisation, for example with a homochiral acid followed by separation of the diastereomeric derivatives by conventional means (e.g. HPLC, chromatography over silica). All stereoisormers are included within the scope of the invention.

Alkyl groups which $R^1$, $R^2$ and $R^3$ may represent may be linear or branched. Typical alkyl groups which may be mentioned include methyl, ethyl, n-propyl, i-propyl, n-butyl i-butyl n-pentyl and i-pentyl and preferred alkyl groups are those wherein $R^2$ and $R^3$ do not both represent ethyl.

Preferred compounds of the invention are those wherein $R^1$ represents n-propyl n-butyl or n-pentyl, $R^2$ represents methyl, ethyl or i-propyl, and $R^3$ represents i-propyl.

More preferred compounds of the invention are those wherein $R^1$ represents n-propyl or n-butyl, $R^2$ represents methyl, ethyl or i-propyl, and $R^3$ represents i-propyl.

Even more preferred compounds of the invention are those wherein $R^1$ represents n-propyl or n-butyl, $R^2$ represents methyl or ethyl, and $R^3$ represents i-propyl.

Especially preferred compounds of the invention are those wherein $R^1$ represents n-propyl $R^2$ represents methyl or ethyl, and $R^3$ represents i-propyl.

Most preferred compounds of the invention are those wherein $R^1$ represents n-propyl, $R^2$ represents methyl, and $R^3$ represents i-propyl.

Preparation

According to the invention there is also provided a process for the preparation of compounds of formula I which comprises:

(a) reaction of a compound of formula II,

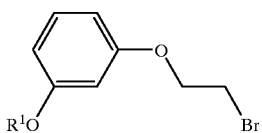

II wherein R¹ is as hereinbefore defined, with a compound of formula III,

 HN(R²)R³    III wherein R² and R³ are as hereinbefore defined, for example at elevated temperature (e.g. reflux) in the presence of a suitable organic solvent (e.g. toluene): or (b) reaction of a compound of formula IV,

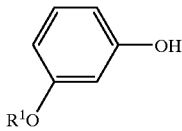

IV wherein R¹ is as hereinbefore defined, with a compound of formula V,

R²(R³)NCH₂CH₂Hal    V wherein Hal represents Cl, Br or I and R² and R³ are as hereinbefore defined, or an acid addition salt thereof, for example at elevated temperature (e.g. reflux) in the presence of a suitable base (e.g. sodium ethoxide) and an appropriate organic solvent (e.g. ethanol).

Compounds of formula II may be prepared analogously to the methods described in U.S. Pat. No 3,105,854 for example by reaction of a compound of formula IV, as hereinbefore defined with a compound of formula VI, HalCH₂CH₂Hal    VI wherein Hal is as hereinbefore defined. Compounds of formula II may be prepared in this way, for example at or around room temperature in the presence of a two phase solvent system and an appropriate ion pair extracting agent. Suitable organic solvents for the two phase system include excess alkyl dihalides of formula VI and suitable ion pair extracting agents include tetrabutylammonium hydroxide.

Compounds of formula IV are commercially available or may be prepared conveniently using known techniques. For example compounds of formula IV may be prepared by the reaction of resorcinol with a compound of formula VII, R¹Hal    VII wherein Hal and R¹ are as hereinbefore defined, for example at elevated temperature (e.g. reflux) in the presence of a suitable base (e.g. sodium ethoxide) and an appropriate organic solvent (e.g. ethanol).

Compounds of formula III, V, VI and VII are either commercially available or are available using known techniques.

The compounds of the invention may be isolated from their reaction mitures using conventional techniques.

Medical and Pharmaceutical Use

The compounds of the invention are useful because they possess pharmacological activity. They are therefore indicated as pharmaceutcals.

According to a further aspect of the invention there is thus provided a compound of formula I as hereinbefore defined, or a pharmaceutically acceptable salt thereof, for use as a pharmaceutical.

In particular, the compounds of the invention possess anaesthetic properties for example as demonstrated in the test described below. They are therefore useful as anaesthetics, in particular local anaesthetics and especially topically applied local anaesthetics.

The compounds of the invention are thus indicated for the treatment of pain, including localised pain.

Pharmaceutical Formulations

The compounds of the invention will normally be administered parenterally, especially topically in the form of pharmaceutical formulations comprising the active ingredient in a pharmaceutically acceptable dosage form.

We prefer administration to be topically to the skin.

Modes of topical administration of the compounds of the invention to the skin which may be mentioned include emulsions, cream, lotions, ointments and skin patches. Compositions comprising the compounds of the invention for topical administration may include other ingredients commonly used in the parenteral administration of pharmaceutically-active compounds.

According to a further aspect of the invention there is thus provided a pharmaceutical formulation including a compound of formula I as, hereinbefore defined, or a pharmaceutically acceptable salt thereof, in admixture with a pharmaceutically acceptable adjuvant, diluent or carrier.

Formulations including the compounds of the invention may be prepared by techniques which are known per se. Usually the active substance will constitute between 0.5 and 15% by weight of the preparation, more specifically between 5 and 10% by weight.

According to a further aspect of the present invention, there is provided a method of treatment of a pain which method comprises administration of a therapeutically effective amount of a compound of formula I as defined above, or a pharmaceutically acceptable salt thereof, to a person suffering from, or susceptible to pain.

The compounds of the invention have the advantage that they can be applied topically to intact skin, and also have a faster onset of action and a longer duration than compounds known in the prior art.

Biological Tests

Test A

Topical Anaesthesia in the Guinea Pig

Topical anaesthesia and analgesia during occlusion of intact skin in the guinea pig was studied by applying lipid formulations of local anaesthetics according to a method similar to that known from J. Pharmacol. Exp. Ther. 85,78 (1945) and detailed below.

Hair was removed from the backs of male guinea pigs (Dunkin-Hartley strain; weight range 300 to 400 g) using a depilatory (Opilca®; Hans Schwarzkopf GmbH, Hamburg, Germany). The hairless smooth skin washed with soap and water and the animal was kept in a cage under a desk lamp for about two hours before further experimentation.

A twitching response was elicited by pricking the skin on the back of the animal with a cannula (22 G; Kifa, no point) or a von Frey filament (4.74; Semmes-Weinstein pressure aesthesiometer). A circular piece of gauze (1 to 8 layer) was saturated with test formulation in a thin plastic cup (4.5 cm²)

and applied to the middle of the back of the animal. The cup was then covered with self-adhesive (Fixomull®; BDF Beirsdorf AG, Hamburg, Germany) and the occlusion was finally protected with an elasticated bandage. Groups of two, three or six animals were used for each test formulation.

The area was treated up to 15 minutes before removing the assembly. The treated area was subsequently wiped with a tissue and then examined for signs of local irritation. The skin which had been in contact with the formulation was pricked with a cannula or a von Frey filament under constant pressure six ties at different places and the presence or absence of twitching response was noted. This procedure was repeated at regular intervals of five minutes.

The number of pricks not eliciting a response gave an indication of the degree of sensory anaesthesia or analgesia. The percentage anaesthesia/analgesia after the actual contact time was expressed as the total number of pricks not eliciting a response as a percentage of the total number of pricks.

EXAMPLES

Starting Materials

Example A 3-(n-Propoxy)phenol

A solution of sodium ethoxide was prepared by adding sodium (11.5 g; 0.5 mol) to ethanol (500 ml). Resorcinol (55 g; 0.5 mol) was added to the stirred resultant solution, followed, half an hour later, by n-propylbromide (67.5 g; 0.55 mol). The reaction mixture was then heated to reflux for 3 hours. Upon cooling the resultant salt was removed by filtration and the solvent was evaporated. The residue was shaken between dilute aqueous sodium hydroxide and ether. The ether phase was extracted with dilute sodium hydroxide and the combined aqueous phases were neutralised using dilute aqueous hydrochloric acid. The precipitated product was extracted with ether, washed with water and dried over magnesium sulphate. Following evaporation, the residue was chromatographed on silica gel using toluene:diisopropylether (2:1) as eluent to yield 27.4 g (36%) of the title compound as an oil (93% purity). The title compound was further purified by distillation. bp 118–120° C. (6 mm Hg) MW=152 (GC-MS)

Example B 3-(n-Butoxy)phenol

Prepared according to the method described in Example A above from resorcinol (55 g; 0.5 mol) and n-butylbromide (75.4 g; 0.55 mol) to yield 32.4 g (39%) of the title compound as an oil (92% purity). bp 148° C. (12 mm Hg) MW=166 (GC-MS)

Example C 3-(n-Pentoxy)phenol

Prepared according to the method described in Example A above from resorcinol (55 g; 0.5 mol) and n-pentylbromide (83.1 g; 0.55 mol) to yield 36.0 g (40%) of the title compound as an oil (92% purity). bp 128–131° C. (5 mm Hg) MW=180 (GC-MS)

Example D 1-(2-Bromoethoxy)-3-n-propoxybenzene

A solution of 3-(n-propoxy)phenol (15.2 g; 0.1 mol; from Example A above) in 1,2-dibromoethane (100 ml; 1.16 mol) was added to a solution of tetrabutylammonium hydrogen sulphate (34 g; 0.1 mol) and sodium hydroxide (8.0 g; 0.2 mol) in water (100 ml). The mixture was stirred vigorously whilst a 50% solution of sodium hydroxide in water (33 ml) was added dropwise over half an hour. Stirring was subsequently continued for one hour. The organic phase was separated, washed with water and dried over magnesium sulphate. The solvent was evaporated and the residue treated with diethyl ether (150 ml). The precipitated salt was removed by filtration and the diethyl ether evaporated. The residue was distilled to yield (14.0 g; 54%) of the title compound as an oil (97% purity). bp 112–115° C. (0.05 mm Hg) MW=259 (GC-MS)

Example E 1-(2-Bromoethoxy)-3-n-butoxybenzene

Prepared analogously to the method described in Example D above from 3-(n-butoxy)phenol (16.6 g; 0.1 mol; from Example B above) and 1,2-dibromoethane (100 ml; 1.16 mol). Following work up, the residue was chromatographed on silica gel with diisopropyl ether as eluent. The resultant oil was distilled to to yield 23.1 g (85%) of the title compound as an oil which subsequently crystallised (98% purity). bp 105–108° C. (0.01 mm Hg) mp 32–34° C. MW=273 (GC-MS)

Example F 1-(2-Bromoethoxy)-3-n-pentoxybenzene

Prepared according to the method described in Example E above from 3-(n-pentoxy)phenol (18.0 g; 0.1 mol; from Example C above) and 1,2-dibromoethane (100 ml; 1.16 mol). Following work up the residue was chromatographed on silica gel with diisopropyl ether as eluent to yield 26.1 g (91%) of the tide compound as an oil which subsequently crystallised (96% purity). MW=287 (GCMS)

General Methods for Preparation of Compounds of Formula I

Method A

Aminoethylation of 3-Alkoxyphenols

A solution of sodium ethoxide was prepared by adding sodium (2.3 g; 0.1 mol) to ethanol (100 ml; 1.63 mol). The appropriate 3-alkoxyphenol (0.05 mol; from Examples A to C above) was added to the resultant solution followed, half an hour's stirring later, by the appropriate 2-dialkylaminoethyl chloride hydrochloride (0.05 mmol) whereupon the reaction mixture was heated under reflux for between 1 and 10 hours. Upon cooling the resultant salt was removed by filtration and the solvent was evaporated. The residue was dissolved in an excess of dilute hydrochloric acid and the acid solution extracted with diethyl ether. The solution was then basified with dilute sodium hydroxide, the product extracted with diethyl ether and the extracts dried over potassium carbonate. The product was purified by distillation in vacuo.

Method B

Amination of 1-(2-Brormoethoxy)-alkoxybenzenes

A mixture of 1-(2-bromoethoxy)-alkoxybenzene (0.04 mol; from Examples D to F above) and the appropriate amine (0.12 mol) in toluene (80 ml) was heated under reflux for between 50 and 1000 hours or to 110° C. in an autoclave for 7 hours. After cooling the resultant salt was removed by filtration and the solvent evaporated. The residue was dissolved in an excess of dilute hydrochloric acid and the acid solution extracted with diethyl ether. The solution was then basified with dilute sodium hydroxide, the product extracted with diethyl ether and the extracts dried over potassium carbonate. The product was purified by distillation in vacuo.

Examples 1 to 9

Compounds of Formula I

The following compounds of formula I were prepared according to the general methods described above:

isopropyl-methyl-[2-(3-n-propoxy-phenoxy)ethyl]-amine (Example 1);

ethyl-isopropyl-[2-(3-n-propoxy-phenoxy)-ethyl]-amine (Example 2);

diisopropyl-[2-(3-n-propoxy-phenoxy)-ethy]-amine (Example 3);

diethyl-[2-(3-n-propoxy-phenoxy)-ethy]-amine (Example 4);

isopropyl-methyl-[2-(3-n-butoxy-phenoxy)-ethyl]-amine (Example 5);

ethyl-isopropyl-[2-(3-n-butoxy-phenoxy)-ethyl]-amine (Example 6);

diisopropyl-[2-(3-n-butoxy-phenoxy)-ethyl]-amine (Example 7);

ethyl-isopropyl-[2-(3-n-pentoxy-phenoxy)-ethly]-amine (Example 8); and diisopropyl-[2-(3-n-pentoxy-phenoxy)-ethyl]-amine (Example 9).

Details of method employed, reaction times, yields and characterising data are given in the Table I below.

Example 10

The compounds of Examples 1 to 9 were an tested in Test A above and were found to exhibit 100% anaesthesia/analgesia using 15 minutes contact time.

TABLE I

| Example | $R^1$ | $R^2$ | $R^3$ | Method | Reaction Time (h) | Yield (%) | bp (° C.) (mm Hg) |
|---|---|---|---|---|---|---|---|
| 1 | $C_3H_7$ | $CH_3$ | $CH(CH_3)_2$ | B | $7^1$ | 73 | 106–109 (0.02) |
| 2 | $C_3H_7$ | $C_2H_5$ | $CH(CH_3)_2$ | B | 120 | 66 | 119–120 (0.05) |
| 3 | $C_3H_7$ | $CH(CH_3)_2$ | $CH(CH_3)_2$ | A | 5 | 62 | 132–136 (0.08) |
| 4 | $C_3H_7$ | $C_2H_5$ | $C_2H_5$ | A | 3 | 35 | 104–107 (0.02) |
| 5 | $C_4H_9$ | $CH_3$ | $CH(CH_3)_2$ | B | $7^1$ | 78 | 114–117 (0.01) |
| 6 | $C_4H_9$ | $C_2H_5$ | $CH(CH_3)_2$ | B | 138 | 72 | 131–134 (0.05) |
| 7 | $C_4H_9$ | $CH(CH_3)_2$ | $CH(CH_3)_2$ | A | 2.5 | 67 | 134–138 (0.04) |
| 8 | $C_5H_{11}$ | $C_2H_5$ | $CH(CH_3)_2$ | B | 3.5 | 77 | 137–140 (0.06) |
| 9 | $C_5H_{11}$ | $CH(CH_3)_2$ | $CH(CH_3)_2$ | B | 476 | 58 | 135–138 (0.02) |

[1]In autoclave

What is claimed is:

1. A compound of formula I,

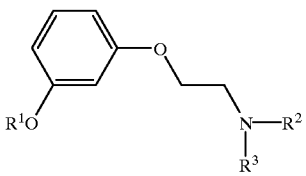

I wherein $R^1$ represents $C_{3-5}$ alkyl; and $R^2$ and $R^3$ independently represent $C_{1-3}$ alkyl;

provided that when $R^2$ and $R^3$ both represent ethyl, then $R^1$ does not represent n-butyl i-butyl or n-pentyl;

or a pharmaceutically acceptable salt thereof.

2. A compound according to claim 1, wherein $R^2$ and $R^3$ do not both represent ethyl.

3. A compound according to claim 1, wherein $R^1$ represents n-propyl, n-butyl or n-pentyl, $R^2$ represents methyl, ethyl or i-propyl and $R^3$ represents i-propyl.

4. A compound according to claim 3, wherein said compound is isopropyl-methyl-[2-(3-n-propoxy-phenoxy)-ethyl]-amine.

5. A compound according to claim 3, wherein said compound is isopropyl-ethyl-[2-(3-n-propoxy-phenoxy)-ethyl]-amine.

6. A compound according to claim 3, wherein said compound is diisopropyl-[2-(3-n-propoxy-phenoxy)-ethyl]-amine.

7. A compound according to claim 3, wherein said compound is isopropyl-methyl-[2-(3-n-butoxy-phenoxy)-ethyl]-amine.

8. A compound according to claim 3, wherein said compound is isopropyl-ethyl-[2-(3-n-butoxy-phenoxy)ethyl]-amine.

9. A compound according to claim 3, wherein said compound is diisopropyl-[2-(3-n-butoxy-phenoxy)-ethyl]-amine.

10. A method according to claim 3, wherein said compound is isopropyl-ethyl-[2-(3-n-pentoxy-phenoxy)-ethyl]-amine.

11. A compound according to claim 3, wherein said compound is diisopropyl-[2-(3-n-pentoxy-phenoxy)-ethyl]-amine.

12. A compound according to claim 1, wherein said compound is diethyl-[2-(3-n-propoxy-phenoxy)-ethyl]-amine.

13. A pharmaceutical composition comprising a compound according to any one of claims 1–3 or 4–12, or a pharmaceutically acceptable salt thereof, in admixture with a pharmaceutically acceptable adjuvant, diluent or carrier.

14. A topical pharmaceutical composition comprising a compound according to any one of claims 1–3 or 4–12, or a pharmaceutically acceptable salt thereof, in admixture with a pharmaceutically acceptably adjuvant, diluent or carrier.

15. A method of providing analgesia or anesthesia to a patient, comprising administering to said patient a therapeutically effective amount of a compound of formula I:

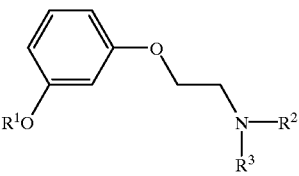

I wherein $R^1$ represents $C_{3-5}$ alkyl; and $R^2$ and $R^3$ independently represent $C_{1-3}$ alkyls;

with the proviso that when $R^2$ and $R^3$ are both ethyl, then $R^1$ is not n-butyl, i-butyl or n-pentyl;

or a pharmaceutically acceptable salt thereof.

16. The method of claim 15, wherein $R^2$ and $R^3$ do not both represent ethyl.

17. The method of claim 15, wherein $R^1$ represents n-propyl, n-butyl or n-pentyl;

$R^2$ represents methyl, ethyl or i-propyl; and $R^3$ represents i-propyl.

18. The method of claim 17, wherein said compound is isopropyl-methyl-[2-(3-n-propoxy-phenoxy)-ethyl]-amine.

19. The method of claim 17, wherein said compound is isopropyl-ethyl-[2-(3-n-propoxy-phenoxy)-ethyl]-amine.

20. The method of claim 17, wherein said compound is diisopropyl-[2-(3-n-propoxy-phenoxy)-ethyl]-amine.

21. The method of claim 17, wherein said compound is isopropyl-methyl-[2-(3-n-butoxy-phenoxy)-ethyl]-amine.

22. The method of claim 17, wherein said compound is isopropyl-ethyl-[2-(3-n-butoxy-phenoxy)-ethyl]-amine.

23. The method of claim 17, wherein said compound is diisopropyl-[2-(3-n-butoxy-phenoxy)-ethyl]-amine.

24. The method of claim 17, wherein said compound is isopropyl-ethyl-[2-(3-n-pentoxy-phenoxy)-ethyl]-amine.

25. The method of claim 17, wherein said compound is diisopropyl-[2-(3-n-pentoxy-phenoxy)-ethyl]-amine.

26. The method of claim 15, wherein said compound is diethyl-[2-(3-n-propoxy-phenoxy)-ethyl]-amine.

27. The method of any one of claims 15–26, wherein said compound provides analgesia to said patient.

28. The method of any one of claims 15–26, wherein said compound provides local anesthesia to said patient.

29. The method of any one of claims 15–26, wherein said compound is administered in a pharmaceutical formulation further comprising a pharmaceutically acceptable adjuvant, diluent or carrier.

30. The method of any one of claims 15–26, wherein said compound is administered topically.

\* \* \* \* \*